US010244481B2

United States Patent
Gliner et al.

(10) Patent No.: US 10,244,481 B2
(45) Date of Patent: Mar. 26, 2019

(54) SYSTEM AND METHOD FOR SWITCHING ON WIRELESS TOOL ONLY WHEN THE LOCATION FREQUENCIES ARE DETECTED

(71) Applicant: Biosense Webster (Israel) Ltd., Yokneam (IL)

(72) Inventors: Vadim Gliner, Haifa (IL); Yaron Ephrath, Karkur (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 16 days.

(21) Appl. No.: 15/479,467

(22) Filed: Apr. 5, 2017

(65) Prior Publication Data

US 2018/0295584 A1    Oct. 11, 2018

(51) Int. Cl.
| | |
|---|---|
| *H04W 52/02* | (2009.01) |
| *H04W 4/02* | (2018.01) |
| *G08B 21/18* | (2006.01) |
| *G01R 19/165* | (2006.01) |
| *H04W 84/12* | (2009.01) |
| *A61B 34/20* | (2016.01) |

(52) U.S. Cl.
CPC .. *H04W 52/0277* (2013.01); *G01R 19/16576* (2013.01); *G08B 21/18* (2013.01); *H04W 4/026* (2013.01); *H04W 52/0245* (2013.01); *A61B 2034/2053* (2016.02); *H04W 84/12* (2013.01)

(58) Field of Classification Search
None
See application file for complete search history.

(56) References Cited

U.S. PATENT DOCUMENTS

| | | | |
|---|---|---|---|
| 6,219,540 B1 | 4/2001 | Besharat et al. | |
| 6,233,476 B1 * | 5/2001 | Strommer | A61B 5/0066 600/424 |
| 6,292,344 B1 * | 9/2001 | Glaser | H02H 7/228 361/111 |
| 6,586,911 B1 * | 7/2003 | Smith | G06F 1/3203 320/134 |
| 2007/0085496 A1 * | 4/2007 | Philipp | A61B 17/151 318/139 |
| 2007/0195784 A1 | 8/2007 | Allen et al. | |
| 2008/0008103 A1 * | 1/2008 | Suzuki | H04L 12/12 370/250 |
| 2008/0058883 A1 * | 3/2008 | Gautier | G06F 1/3203 607/29 |

(Continued)

*Primary Examiner* — Hong S Cho
(74) *Attorney, Agent, or Firm* — Volpe and Koenig, P.C.

(57) ABSTRACT

A power management method and system for switching on a wireless tool when location frequencies are detected, and subsequently invoking a low-powered hibernation mode when location frequencies are not detected. The method and system include a wireless tool configured to emit a mixed electromagnetic frequency signal, and a processor configured to acquire a mixed signal and determine a voltage, set the wireless tool to a hibernation mode when the voltage is below a predetermined amount, and set the wireless tool to an active mode and apply an algorithm to calculate the location and orientation of the wireless tool when the voltage is above the predetermined amount. The system and method thus allow for conservation of battery power of the wireless tool, improving the battery life of the wireless tool and increasing procedural efficiency.

16 Claims, 4 Drawing Sheets

(56) References Cited

U.S. PATENT DOCUMENTS

| | | | |
|---|---|---|---|
| 2008/0303785 A1* | 12/2008 | Yun | G06F 3/14 |
| | | | 345/156 |
| 2009/0018653 A1* | 1/2009 | Bashiri | A61B 17/12022 |
| | | | 623/11.11 |
| 2011/0183726 A1 | 7/2011 | Deng | |
| 2011/0207509 A1 | 8/2011 | Crawford | |
| 2014/0107471 A1* | 4/2014 | Haider | A61B 17/1703 |
| | | | 600/424 |

* cited by examiner

SYSTEM AND METHOD FOR SWITCHING ON WIRELESS TOOL ONLY WHEN THE LOCATION FREQUENCIES ARE DETECTED

FIELD OF INVENTION

The present invention relates generally to managing power for wireless tools, and more specifically to extending battery life and power of a battery-operated wireless tool by switching the tools on or off based on location detection.

BACKGROUND

Non-fixed medical tools are used for a variety of critical health procedures and require a highly reliable power management system to prevent power failure. Medical systems traditionally transmit signals to connect with non-fixed medical tools and to receive a constant and reliable power source to the non-fixed tool over a fixed wire or cable. These non-fixed wired systems and tools employed a fixed wire connection to receive a constant reliable source of power. The advancement of short-range radio technology now affords medical tool manufacturers the ability to create non-fixed tools without the need for a fixed physical cable. For example, non-fixed tools meeting or complying with the Institute of Electrical and Electronics Engineers (IEEE) 802.11g, IrDA (infrared data), and Ericsson Bluetooth™ specifications provide short-range radio technology to enable wireless communications.

Current non-fixed wireless tools, however, do not include a fixed continuous reliable power source. Instead, the tools rely on a portable battery power source, typically with a finite life of about three to four hours, for operation when active. Thus, if the battery is not charged or properly recharged, it could fail (i.e. run out of charge) during a procedure. Due to the critical health support requirements for these medical tools and the potential consequences of a power failure in such equipment, the tools therefore require a highly reliable battery power management system.

These battery-operated wireless tools, when used under normal operation, are exposed to functional issues. One example of a functional issue is that manufacturers of medical tools seek to create tools that are as small and light as possible for use in specific medical procedures, especially in ENT procedures. On the other hand, the battery-operated wireless tool must maintain power as long as possible, which requires the application of a larger-sized battery.

Another example of a functional issue is providing wireless location indication at all times to the user. During a surgical or medical procedure, a physician may use numerous wireless tools, but will not use all of those tools for the entirety of the procedure. Instead, a physician typically uses a battery-operated wireless tool for a specific period of time and then puts it aside and uses other wireless tools for other portions of the procedure, and may use the battery-operated wireless tool again at a later period. Thus, battery-operated wireless tools that are not in use by the physician for a period of time during the procedure are still on and constantly providing an indication of the tool's location and/or status. This poses a particular challenge for power management, since the battery of the battery-operated wireless tool has a finite life and power is constantly decreasing as the tool is on and providing the tool's location, even during non-use. Moreover, physicians are not interested in location indication of wireless tools that are set aside during a procedure; instead, physicians prefer location indication of the tool that they are currently using.

Thus, it would be advantageous to offer a system that extends the battery life of a battery-operated wireless tool by switching on the wireless tool when location frequencies are detected, and subsequently invoking a low-powered hibernation or other power saving mode when location frequencies are not detected to ensure proper and extended wireless tool operation during procedures.

SUMMARY

A method and system for managing power of a wireless tool is provided. The method comprises acquiring a mixed electromagnetic frequency signal emitted by a location pad for electromagnetic navigation purposes and determining a voltage based on the signal; setting the wireless tool to a hibernation mode when the voltage is below the predetermined amount because the tool is far away from navigational space and thus does not need to be navigated; and setting the wireless tool to an active mode and applying an algorithm to calculate the location and orientation of the wireless tool when the voltage is above the predetermined amount. The system comprises a location pad comprising at least one field generator, a wireless tool configured to receive a mixed electromagnetic frequency signal, and a processor configured to analyze a mixed signal and determine a voltage, set the wireless tool to a hibernation mode when the voltage is below a predetermined amount, and set the wireless tool to an active mode and apply an algorithm to calculate the location and orientation of the wireless tool when the voltage is above the predetermined amount.

BRIEF DESCRIPTION OF THE DRAWINGS

The present invention is illustrated by way of example, and not by way of limitation, in the figures of the accompanying drawings in which.

DETAILED DESCRIPTION OF THE PREFERRED EMBODIMENT

A system and method for switching on a wireless tool and switching the wireless tool to a low power or hibernation mode when location frequencies are detected is presented.

Figure 1:
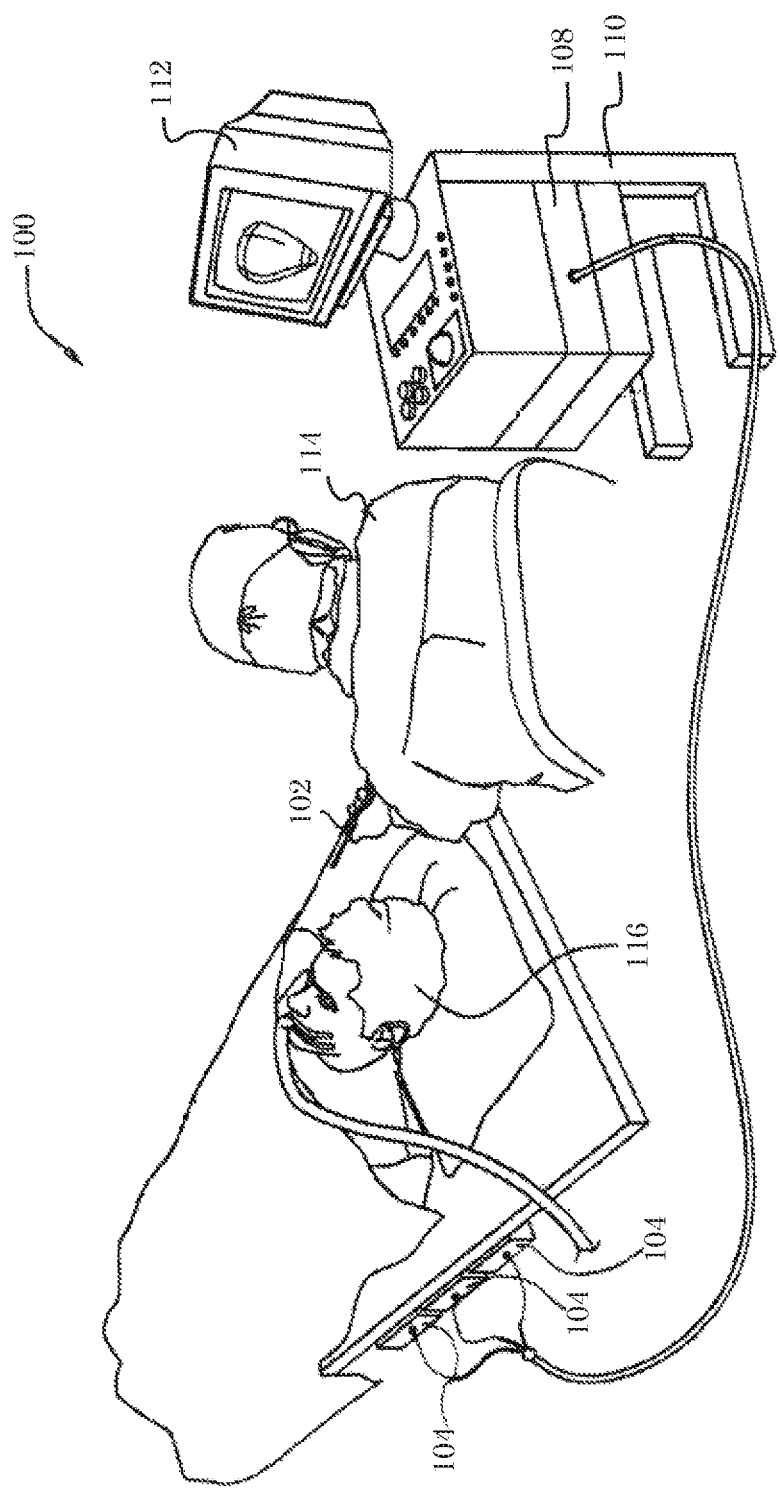
FIG. 1 is a schematic diagram of a power management system for a wireless tool in accordance with an embodiment of the present invention.

FIG. 1 illustrates a schematic diagram of the power management system 100 for a wireless tool in accordance with an embodiment of the present invention. The power management system 100 includes a wireless tool 102, a location pad comprising at least one field generator 104, a processor 108, a console 110 and a display or monitor 112. The wireless tool 102 can be a wireless medical tool. The monitor 112 can be attached to the console 110 or can be mounted separately from the console 110.

As shown in FIG. 1, an individual 114, such as a physician, operates the system 100 to perform a medical procedure on a patient 116. The physician 114 uses the wireless tool 102 when performing a portion of the medical procedure. During other portions of the medical procedure, the wireless tool 102 is not used.

In one embodiment, the location pad 104 may comprise one field generator. In another embodiment, the location pad 104 may comprise multiple field generators. Each field generator may include multiple coils (not shown) that, during a medical procedure, emit electromagnetic fields, each of its own frequency, and one or more sensors (not shown) that detect the frequencies emitted. The system uses the electromagnetic fields generated by the field generators 104 and detected by the sensors to, among other things, calculate and determine the location of a tool in three-dimensional space. When the tool 102 is not in use, the system may detect an "out of range" location of the tool 102, e.g., a location that is not in accordance with use of the tool 102, and switch the tool 102 to a hibernation mode because the tool is far away from navigational space and thus does not need to be navigated. The system calculates whether signal amplitude from the tool 102 does or does not exceed a certain frequency threshold. If the frequency threshold is exceeded, the tool 102 is in position to be used. If the tool 102 had been in hibernation mode, and it now exceeds the threshold, the tool 102 is switched on or activated. Throughout the medical procedure, when the frequency threshold is exceeded, the wireless tool 102 remains active or in use. Otherwise, when the frequency threshold is less than a predetermined threshold, the wireless tool 102 is switched to and maintained in hibernation mode.

Figure 2A:
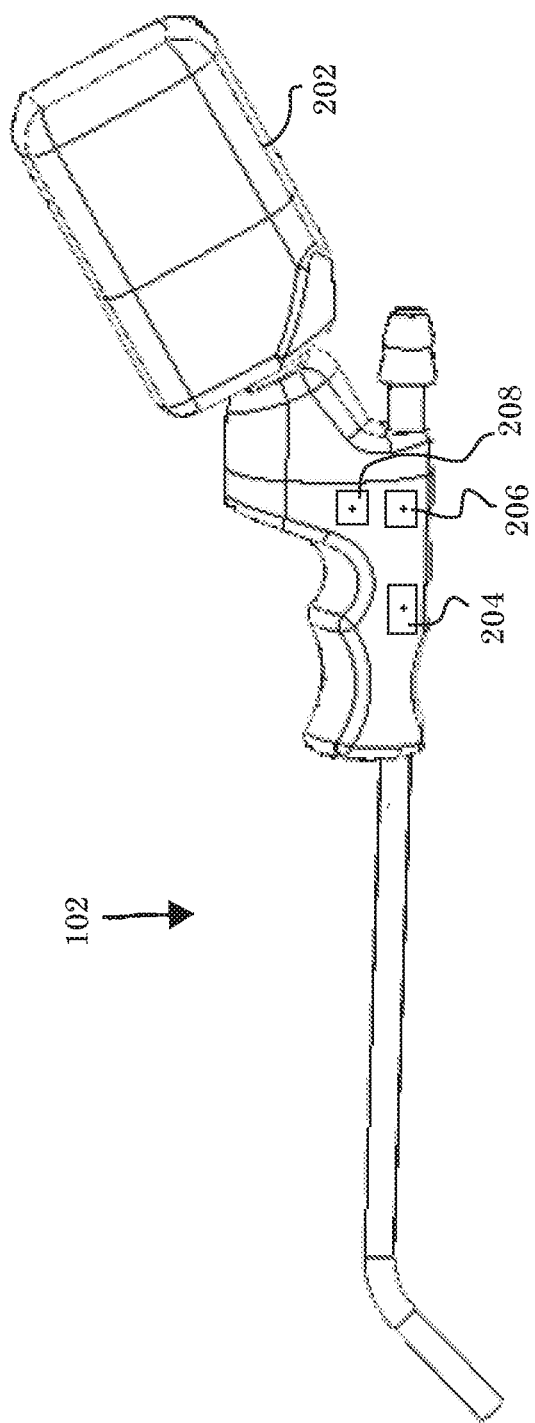
FIG. 2A is an exemplary wireless tool of the power management system.

FIG. 2A shows an exemplary wireless tool 102. In one embodiment, the wireless tool 102 may be a wireless medical tool. The wireless tool 102 may obtain power by one or more batteries via a battery pack or battery holder 202. Current wireless tools provide short-range radio technology to enable wireless communications. These technologies enable the wireless transmission and receiving of signals; however, they cause significant power consumption by the tool. The present system aims to conserve and manage power, by limiting power consumption from wireless communications by switching to a low power mode during non-use of the wireless tool 102. The low power mode enables reduction of battery consumption to preserve and extend the duration of usage of the tool.

The wireless tool 102 can comprise a detection mechanism comprising an inductor 204 and resistors 206, 208 for transmitting signals including voltage, to the processor 108, as shown in FIG. 1. During a medical procedure, the wireless tool 102 receives electromagnetic fields with specific frequency signals ("magnetic location frequencies") for purposes of magnetic navigation. In the present embodiment, the frequencies may range from 17 kilohertz (kHz) to 19.8 kHz. In other embodiments, the frequencies may be higher or lower in value. The inductor 204 receives the signals and is tuned with a capacitor to the specific frequency of the location. The inductor 204 is passive and thus does not consume power. When the signal received by the inductor 204 is not at magnetic location frequencies, the coil is discharged through resistor 206, and the voltage on resistor 208 is very low. This voltage signal is sent to the processor 108, as shown in FIG. 1, and the processor 108 analyzes the signal and maintains the wireless tool 102 in a hibernation mode.

When the wireless tool 102 is moved to a location where it will be used, the voltage on resistor 208 increases and exceeds the frequency threshold. This voltage signal is sent to the processor 108, as shown in FIG. 1, which causes the wireless tool 102 to be enabled or activated to an active power mode. When the wireless tool 102 is enabled, the processor 108 communicates with the wireless tool 102 via wireless frequency (WiFi) and the processor 108 calculates the location of the wireless tool 102 and its orientation in space.

The hibernation mode may include not transmitting or receiving wireless communications between the wireless tool 102 and the processor 108, as well as an overall reduced power during periods of non-use of the wireless tool 102. Other reduced power management schemes may be employed. In hibernation mode, wireless communication can be limited to location detection only.

Furthermore, the wireless tool 102 may generate either a visible or audible indication to indicate sufficient battery power is available. A visible indication may include an illuminating light emitting diode (LED) and/or an indicator on the monitor 112, while an audible indication may include a periodically sounding audible tone. The audible indication may be produced through speakers (not shown) in the console 110. A visible or audible indication may also be used to indicate when the battery power falls below a certain threshold.

Figure 2B:
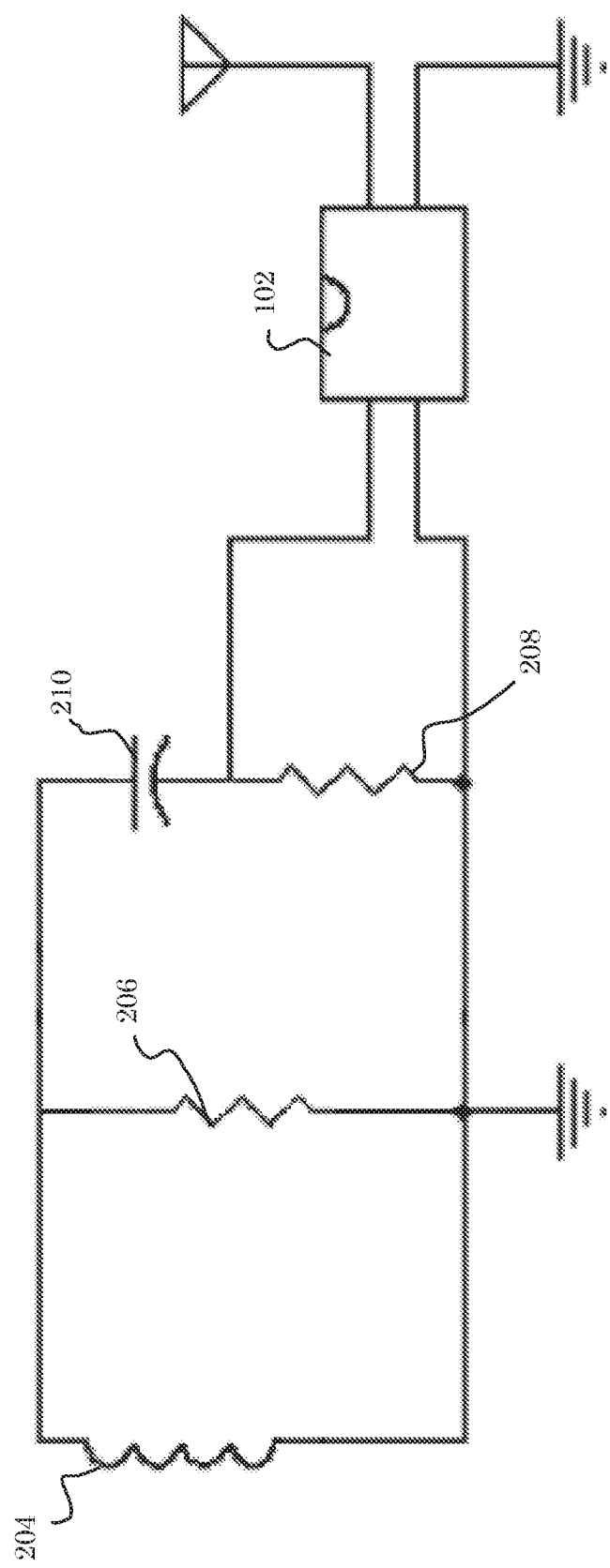
FIG. 2B is an electrical diagram of an embodiment of the power management system.

FIG. 2B is an electrical diagram of an embodiment of the power management system. In the present embodiment, the inductor 204 receives the frequency signals emitted by the location pad 104 and is tuned with a capacitor 210 to the specific frequency of the location. When the signal received by the inductor 204 is not at magnetic location frequencies, the coil is discharged through resistor 206, and the voltage on resistor 208 is very low. The wireless tool 102 is thus maintained in a hibernation mode.

When the wireless tool 102 is moved to a location where it will be used, e.g., inductor 204 matches the specific frequency of the capacitor 210 of the location, the voltage on resistor 208 increases and exceeds the frequency threshold, which causes the wireless tool 102 to be enabled or activated to an active power mode. Otherwise, while the voltage remains low, the wireless tool 102 remains in hibernation mode. Maintaining the wireless tool 102 in a hibernation mode during non-use and activating or enabling the wireless tool 102 when it is moved to a location where it will be used thus conserves battery power and prolongs the life of the wireless tool 102. This configuration may also allow a smaller battery to be used in the wireless tool 102, since less battery power is required to maintain the wireless tool during a procedure.

Figure 3:
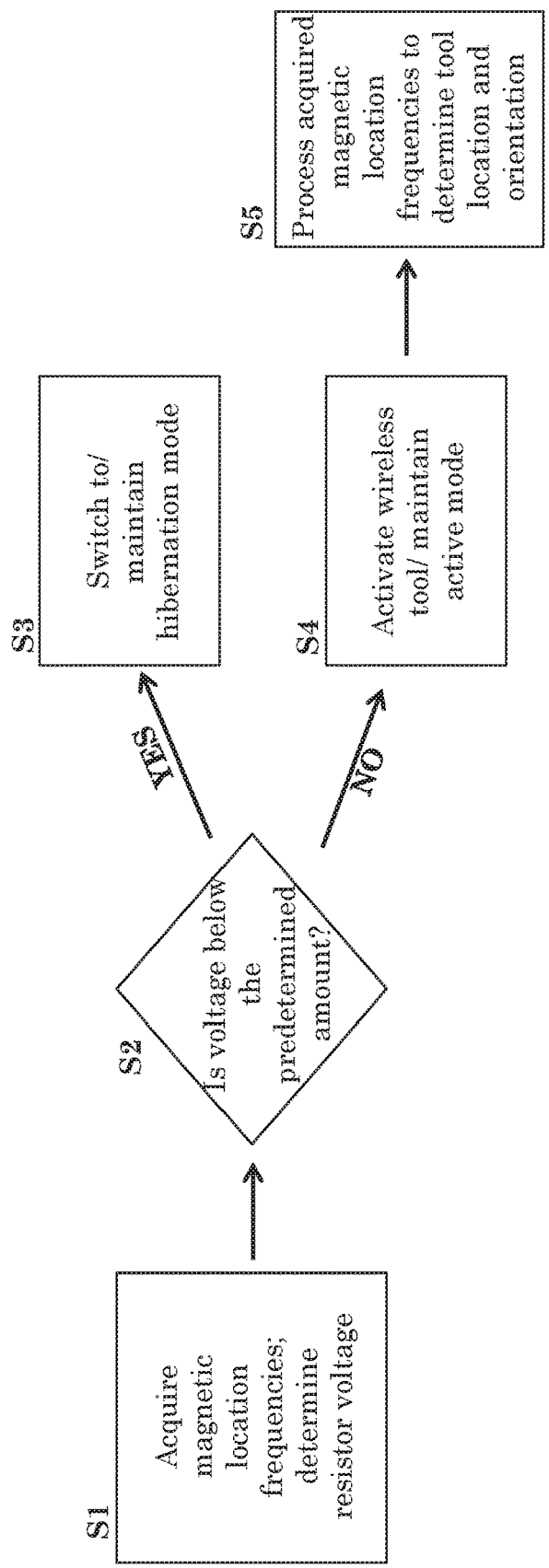
FIG. 3 is a flow diagram of a method for activating a power mode and/or a hibernation mode of a wireless tool in accordance with an embodiment of the present invention.

FIG. 3 is a flow diagram of an embodiment of the inventive method for switching on a wireless tool when location frequencies are detected. This procedure is typically performed during a medical procedure. In step S1, the wireless tool 102 receives the magnetic location frequencies emitted by the location pad 104 via the inductor 204, so that the coil is discharged through a first resistor 206 and affects the voltage of the second resistor 208. In step S2, the voltage is compared to a predetermined amount. If this voltage is below the predetermined amount (S2=YES), then the system recognizes that the tool is inactive. In step S3, the tool is switched to or maintained in hibernation mode and the system continues to monitor the tool by returning to step S1. If the voltage of resistor 208 is not less than the predetermined amount (S2=NO), then in step S4, the processor 108 activates the wireless tool 102 to an active power mode.

In step S5, the acquired mixed signal from step S1 is processed by the processor 108 to determine the frequencies emitted by each respective coil. In one embodiment, in step S5 the processor 108 applies an algorithm to detect the signal amplitude above a certain frequency threshold. Every reception mode provides the possibility of noise or other unwanted input signals besides the desired signals, so different detection approaches may be used. In one embodiment, the algorithm applied by the processor 108, to determine the location and orientation of the wireless tool 102 in three-dimensional space, is the Goertzel algorithm. In addition, the processor 108 communicates with the tool via WiFi.

One problem with discrete Fourier transforms (DFT) and fast Fourier transforms is that it is not very efficient to estimate the Fourier transform coefficients at a small number of frequencies although it is very efficient to estimate the coefficients at larger number of frequencies. This problem can be overcome by evaluating samples at the actual dual-tone multi-frequency (DTMF) frequencies using a non-uniform DFT. One example of a non-uniform DFT is the Goertzel algorithm. In contrast to Fast Fourier Transformation (FFT), the Goertzel algorithm can always be employed if a known, discrete frequency is to be analyzed. This is typically the case in the detection mechanism of the present invention.

It should be understood that many variations are possible based on the disclosure herein. Although features and elements are described above in particular combinations, each feature or element can be used alone without the other features and elements or in various combinations with or without other features and elements.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media).

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method for managing power of a wireless tool, comprising:
    acquiring a mixed signal comprising a plurality of frequencies from at least one field generator and determining a voltage of the signal based on a distance of the wireless tool from the at least one field generator, wherein the voltage decreases as the distance of the wireless tool from the at least one field generator increases and the voltage increases as the distance of the wireless tool from the at least one field generator decreases;
    when the wireless tool is at a distance from the at least one field generator where the voltage is below a predetermined amount, setting the wireless tool to a hibernation mode; and
    when the wireless tool is at a distance from the at least one field generator where the voltage is above the predetermined amount, setting the wireless tool to an active mode and applying an algorithm to calculate the distance of the wireless tool from the at least one field generator.

2. The method according to claim 1, further comprising: using a resistor to determine the voltage.

3. The method according to claim 1, wherein the hibernation mode comprises signal detection only.

4. The method according to claim 1, wherein the active mode enables wireless communication transmittance.

5. The method according to claim 1, wherein the algorithm is the Goertzel algorithm.

6. A system for managing power of a wireless tool, comprising:
    a wireless tool;
    at least one field generator; and
    a processor configured to:
        analyze a mixed signal comprising a plurality of frequencies from the at least one field generator and determine a voltage of the signal based on a distance of the wireless tool from the at least one field generator, wherein the voltage decreases as the distance of the wireless tool from the at least one field generator increases and the voltage increases as the distance of the wireless tool from the at least one field generator decreases;
        when the wireless tool is at a distance from the at least one field generator where the voltage is below a predetermined amount, set the wireless tool to a hibernation mode; and
        when the wireless tool is at a distance from the at least one field generator where the voltage is above the predetermined amount, set the wireless tool to an active mode and apply an algorithm to calculate the distance of the wireless tool from the at least one field generator.

7. The system according to claim 6, further comprising a monitor displaying an indicator indicating the hibernation mode is set.

8. The system according to claim 6, wherein the wireless tool further comprises:
    at least one inductor,
    at least one capacitor, and
    at least one resistor.

9. The system according to claim 8, wherein the inductor is tuned with the capacitor to a specific frequency of the location of the wireless tool.

10. The system according to claim 9, wherein the inductor is configured to receive frequency signals emitted by the at least one field generator.

11. The system according to claim 8, wherein the resistor is configured to transmit voltage signals.

12. The system according to claim 6, wherein the system further comprises an audible indication of battery power of the wireless tool.

13. The system according to claim 6, wherein the system further comprises a visible indication of battery power of the wireless tool.

14. The system according to claim 6, wherein the hibernation mode includes signal detection only.

15. The system according to claim 6, wherein the active mode enables wireless communication transmittance.

16. A computer software product, including a non-transitory computer readable storage medium in which computer program instructions are stored, which instructions, when executed by a computer, cause the computer to perform the steps of:
- acquiring a mixed signal comprising a plurality of frequencies from at least one field generator and determining a voltage of the signal based on a distance of a wireless tool from the at least one field generator, wherein the voltage decreases as the distance of the wireless tool from the at least one field generator increases and the voltage increases as the distance of the wireless tool from the at least one field generator decreases;
- when the wireless tool is at a distance from the at least one field generator where the voltage is below a predetermined amount, setting the wireless tool to a hibernation mode; and
- when the wireless tool is at a distance from the at least one field generator where the voltage is above the predetermined amount, setting the wireless tool to an active mode and applying an algorithm to calculate the distance of the wireless tool from the at least one field generator.

\* \* \* \* \*